United States Patent [19]
Haramaki et al.

[11] Patent Number: 5,872,288
[45] Date of Patent: Feb. 16, 1999

[54] PROCESS FOR PRODUCING (METH) ACRYLIC ACID

[75] Inventors: Hidefumi Haramaki, Himeji; Osamu Dodo, Hyogo-ken; Mamoru Takamura, Takasago, all of Japan

[73] Assignee: Nippon Shokubai Co., Ltd., Osaka, Japan

[21] Appl. No.: 990,522

[22] Filed: Dec. 15, 1997

[30] Foreign Application Priority Data

Dec. 16, 1996 [JP] Japan .................................... 8-335593

[51] Int. Cl.$^6$ .................................... C07C 51/42
[52] U.S. Cl. .................................... 562/600; 203/DIG. 21
[58] Field of Search ...................... 562/600; 203/DIG. 21

[56] References Cited

U.S. PATENT DOCUMENTS

| | | | |
|---|---|---|---|
| 4,618,709 | 10/1986 | Sada et al. | 562/532 |
| 4,987,252 | 1/1991 | Kuragano et al. | 562/600 |

FOREIGN PATENT DOCUMENTS

| | | |
|---|---|---|
| 0023774 | 2/1981 | European Pat. Off. . |
| 0132450 | 2/1985 | European Pat. Off. . |
| 0297788 | 1/1989 | European Pat. Off. . |
| 60-16927 | 4/1985 | Japan . |
| 62-45218 | 9/1987 | Japan . |
| 407118198 | 5/1995 | Japan . |
| 7-80810 | 8/1995 | Japan . |
| 2004886 | 4/1979 | United Kingdom . |

OTHER PUBLICATIONS

Database WPI, Section Ch, Week 9532, Derwent Publications Ltd., London GB Abstract of Jap. Laid–Open Patent Appln. Publ. No. 1–226845 (Sep. 11, 1989).

*Primary Examiner*—Gary Geist
*Assistant Examiner*—Rosalynd Keys
*Attorney, Agent, or Firm*—Sherman and Shalloway

[57] ABSTRACT

The present invention provides a process for producing (meth)acrylic acid by gas-phase catalytic oxidation, which comprises cooling and condensing a (meth)acrylic acid-containing reaction product gas to obtain a crude aqueous (meth)acrylic acid solution; cooling the aqueous solution to deposit the impurities contained in the aqueous solution, as solid matter; separating the solid matter; and then extracting and separating (meth)acrylic acid from the purified aqueous (meth)acrylic acid solution obtained. Unlike the conventional processes in which (meth)acrylic acid is extracted and separated from a crude aqueous (meth)acrylic acid solution, the present process can avoid various troubles caused by the impurities contained in the crude aqueous (meth)acrylic acid solution, for example, generation of scum and the like, and therefore can produce (meth)acrylic acid at a higher purity than in the conventional processes.

5 Claims, 3 Drawing Sheets

PROCESS FOR PRODUCING (METH) ACRYLIC ACID

The present invention relates to a process for producing (meth)acrylic acid. More particularly, it relates to a process for producing (meth)acrylic acid by gas-phase catalytic oxidation, wherein troubles such as generation of scum and the like are effectively prevented and (meth)acrylic acid of high purity is produced efficiently.

In the production of methacrylic acid by the gas-phase catalytic oxidation of isobutylene, tert-butanol, methacrolein or isobutyl aldehyde, an aqueous methacrylic acid solution obtained by cooling and condensing a methacrylic acid-containing reaction product gas is freed of such low-boiling substances as methacrolein and the like and thereafter introduced into a solvent-extraction column to extract and separate methacrylic acid, and the separated methacrylic acid is further purified by distillation or the like to obtain a methacrylic acid product.

In the methacrylic acid-containing reaction product gas, there are contained, in addition to methacrylic acid, various by-products, for example, aromatic carboxylic acids such as terephthalic acid and the like; maleic acid, aldehydes, polymers; and so forth. These by-products, especially terephthalic acid, cause, in the extraction and separation step for extracting and separating methacrylic acid from the aqueous methacrylic acid solution and the distillation step for purifying the separated methacrylic acid, various troubles such as the attachment of by-products to the wall of vessel, the generation of scum, the acceleration of polymerization of methacrylic acid, the reduction of yield of methacrylic acid, and the like.

As techniques for solving the above problems, there have been known a method which comprises contacting an aqueous methacrylic acid solution with a solvent, prior to the introduction of the solution into a solvent-extraction column, separating the deposited polymer and thereafter introducing the polymer-freed, aqueous methacrylic acid solution into the solvent-extraction column (Japanese Patent Publication No. 16,927/1985); a method which comprises adding a bisulfite to an aqueous methacrylic acid solution and feeding the resulting mixture to an extraction step (Japanese Patent Publication No. 45,218/1987); a method which comprises adding to an aqueous methacrylic acid solution an organic compound such as an aromatic carboxylic acid or the like and/or a metal powder to deposit the organic compounds (e.g. terephthalic acid) contained in the aqueous methacrylic acid solution and thereafter separating the deposited organic compounds (Japanese Patent Publication No. 80,810/1995); and so forth.

Further, in the production of acrylic acid by gas-phase catalytic oxidation of propylene or the like, there has been carried out a method which comprises cooling and condensing an acrylic acid-containing reaction product gas to obtain an acrylic acid-containing solution, and subjecting the solution to solvent extraction to separate acrylic acid.

After the extraction and separation of methacrylic acid from an aqueous methacrylic acid solution, it is necessary to treat the resulting waste water, and the amount of this waste water is desired to be as small as possible in view of, for example, the energy cost and apparatus size required for the treatment of the waste water. In order to make the amount of the waste water small, it is necessary to decrease the amount of water used in the step of cooling and condensing the methacrylic acid-containing reaction product gas so as to obtain an aqueous methacrylic acid solution having a high methacrylic acid concentration. When the requirement in treatment of waste water, the recovery of methacrylic acid from the methacrylic acid-containing reaction product gas, and the like are considered, it is preferable to control the concentration of methacrylic acid in the aqueous methacrylic acid solution at 35 to 50% by weight.

Generally, when the methacrylic acid concentration in the aqueous methacrylic acid solution is higher, the solubility of terephthalic acid or the like in the aqueous methacrylic acid solution is higher. Therefore, according to the conventional method, it is difficult to sufficiently deposit, before the extraction step, terephthalic acid or the like which is low in deposition rate. As a result, when such an aqueous methacrylic acid solution is introduced into an extraction column to contact it with a solvent, a large amount of scum is generated, which tends to invite troubles.

Accordingly, an object of the present invention is to provide a process for producing methacrylic acid, wherein the impurities contained in an aqueous methacrylic acid solution are efficiently removed in a simple manner without using a solvent, an organic compound, a metal powder, etc. as in the above-mentioned conventional methods and, thereby, the above-mentioned troubles due to the impurities are effectively prevented to make it possible to efficiently and stably extract and separate methacrylic acid from the aqueous methacrylic acid solution.

Another object of the present invention is to provide a process for removing impurities efficiently from an aqueous methacrylic acid solution having a high methacrylic acid concentration of 35 to 50% by weight in a simple manner.

A still another object of the present invention is to provide a process for producing acrylic acid wherein acrylic acid can be efficiently extracted and separated from an aqueous acrylic acid solution with no troubles caused by impurities.

Incidentally, in the present invention, acrylic acid and methacrylic acid are collectively referred to as (meth)acrylic acid.

The present inventors have made extensive research for achieving the above objects and have consequently found that when a crude aqueous (meth)acrylic acid solution obtained by cooling and condensing a (meth)acrylic acid-containing reaction product gas is cooled, the above-mentioned impurities are deposited as solid matter and can easily be removed.

Thus, according to the present invention, there is provided a process for producing (meth)acrylic acid by gas-phase catalytic oxidation, which comprises cooling and condensing a (meth)acrylic acid-containing reaction product gas to obtain a crude aqueous (meth)acrylic acid solution; cooling the aqueous solution to deposit the impurities contained in the aqueous solution, as solid matter; separating the solid matter; and then extracting and separating (meth)acrylic acid from the purified aqueous (meth)acrylic acid solution obtained.

The present invention is explained in more detail below for a case of producing methacrylic acid.

The process for producing methacrylic acid comprises basically a step of the gas-phase catalytic oxidation of isobutylene, tert-butanol, methacrolein or isobutyl aldehyde; a cooling and condensation step in which the methacrylic acid-containing reaction product gas obtained in the gas-phase catalytic oxidation step is cooled and condensed to obtain a crude aqueous methacrylic acid solution; and an extraction and separation step in which the crude aqueous methacrylic acid solution is, if necessary, freed of low-boiling substances by distillation or stripping and then is subjected to extraction of methacrylic acid by the use of an extracting agent to separate methacrylic acid. The present invention is an improvement of this basic process, and is characterized by subjecting the crude aqueous methacrylic acid solution to purification step prior to the step of extracting and separating methacrylic acid. The purification step consists of cooling the crude aqueous methacrylic acid solution to deposit, as solid matter, the impurities contained in the aqueous solution and removing the deposited solid matter from the aqueous solution. In the present invention, from the solid matter-free, purified aqueous methacrylic acid solution obtained in the purification step, methacrylic acid is extracted and separated in the subsequent extraction and separation step.

Incidentally, as generally adopted in the production of methacrylic acid, it is a matter of course that a distillation step may be provided after the extraction and separation step to purify methacrylic acid. In addition, each of the above-mentioned gas-phase catalytic oxidation step, the cooling and condensation step, the purification step and the extraction and separation step can be conducted in a manner known per se, and the method, conditions, apparatus and the like therefor are not critical.

According to the process of the present invention, the crude aqueous methacrylic acid solution is introduced into a mixing vessel and cooled therein at a temperature ranging from 5° to 50° C., preferably from 20° to 40° C., usually under normal pressure. Incidentally, this cooling had better be conducted with sufficient agitation of the aqueous solution. The residence time in the mixing vessel is varied depending upon the cooling temperature and the like and hence cannot be specified in a given range. However, it is usually 1 to 30 hours, preferably 2 to 5 hours. The solid matter deposited upon cooling is taken out together with the aqueous solution from the mixing vessel and thereafter separated by a separating means such as filter or the like.

BRIEF DESCRIPTION OF DRAWINGS

In the accompanying drawings.

In each figure, 1 to 9 refer to lines, A to a mixing vessel, B to a cooling and mixing vessel, C to a separation apparatus and D to an extraction column.

The above-mentioned process of the present invention is further explained below based on FIG. 1. A crude aqueous methacrylic acid solution is introduced into the mixing vessel A through the line 1 and cooled, whereby solid matter is deposited; the solution containing the solid matter is introduced into the separation apparatus C through the line 2. In the separation apparatus C, the solid matter is separated and then taken out through the line 4. The purified aqueous methacrylic acid solution from which the solid matter has been separated, is introduced into the extraction column D through the line 3 and subjected to extraction and separation therein.

In the present invention, when the crude aqueous methacrylic acid solution is cooled to deposit solid matter, it is suitable for effectively conducting the deposition of the solid matter that a part of the aqueous solution is introduced into a cooling and mixing vessel, the solid matter is deposited therein, and the solid matter-containing aqueous solution obtained is circulated to a mixing vessel. This suitable process is shown in FIGS. 2 to 5.

Figure 2:
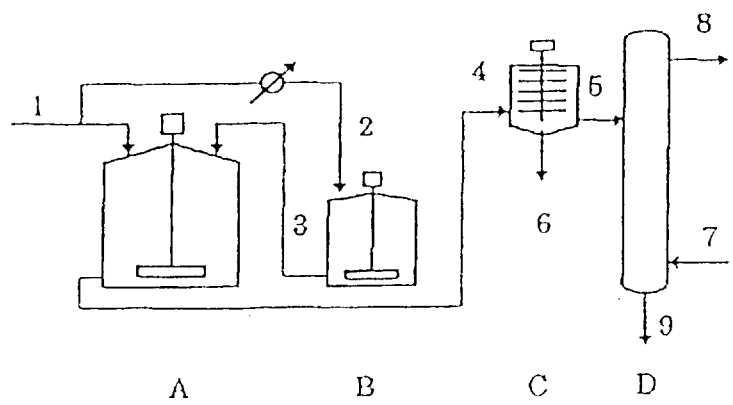

According to the process shown in FIG. 2, most of the crude aqueous methacrylic acid solution fed from the line 1 is introduced into the mixing vessel A, and the remaining portion, usually 3 to 30% by weight, preferably 5 to 10% by weight, of the crude aqueous methacrylic acid solution is introduced into the cooling and mixing vessel B through the line 2. In the cooling and mixing vessel B, the solution is cooled at a temperature ranging from 0° to 30° C., preferably from 5° to 10° C., usually under normal pressure, and the solution containing the deposited solid matter is circulated to the mixing vessel A through the line 3. The residence time in the cooling and mixing vessel B is varied depending upon the cooling temperature and the like and hence cannot be specified in a given range specified; however, it is usually 5 to 25 hours, preferably 10 to 20 hours.

In the mixing vessel A, a mixture of the aqueous solution introduced through the line 1 and the solid matter-containing aqueous solution circulated through the line 3 is stirred usually under normal pressure. Incidentally, the temperature of the solution introduced through the line 1 is usually in the range of from 55° to 70° C., and upon mixing this solution with the solid matter-containing aqueous solution circulated from the cooling and mixing vessel B, the temperature of the mixture is substantially in the range of from 20° to 50° C., preferably from 30° to 40° C., so that the stirring in the mixing vessel A is conducted in this temperature range.

The residence time in the mixing vessel A is varied depending upon the stirring temperature and the like and hence cannot be specified in a given ; however, it is usually 1 to 30 hours, preferably 2 to 5 hours.

Thus, by depositing the solid matter in the cooling and mixing vessel B and utilizing the same as seed crystal, it is possible to accelerate the deposition and growth of solid matter in the mixing vessel A. This process makes it possible to lower the cooling temperature in the mixing vessel A which has a larger volume than that of the cooling and mixing vessel B, and hence, the energy cost can be reduced as compared with the process in which the solid matter is deposited only in the mixing vessel A.

Figure 3:
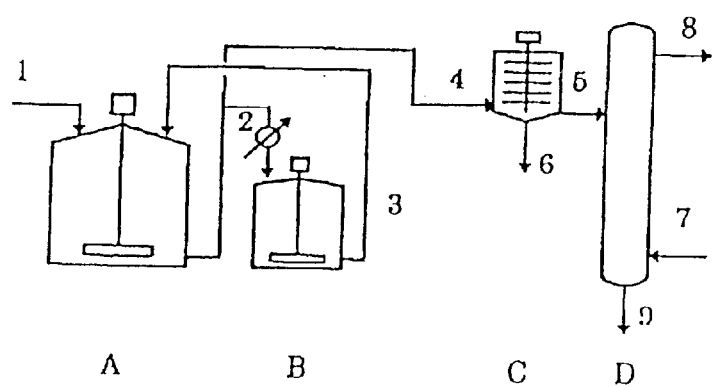

According to the process shown in FIG. 3, into the mixing vessel A are introduced the crude aqueous methacrylic acid solution through the line 1 and the solid matter-containing aqueous solution from the cooling and mixing vessel B through the line 3. The aqueous solution containing the solid matter deposited in the mixing vessel A is sent to the separation apparatus C through the line 4. In this case, a part, usually 3 to 30% by weight, preferably 5 to 10% by weight, of the solid matter-containing aqueous solution in the line 4 is introduced into the cooling and mixing vessel B through the line 2. In the cooling and mixing vessel B, the solid-containing aqueous solution is cooled at 0° to 30° C., preferably 5° to 10° C., and thereafter circulated to the mixing vessel A through the line 3. Incidentally, the temperatures and residence times in the mixing vessel A and the cooling and mixing vessel B are the same as described above in the process of FIG. 2.

Figure 4:
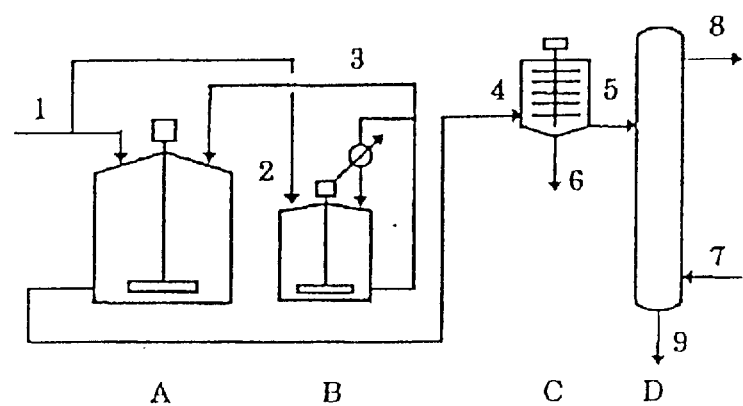

The process shown in FIG. 4 is a partial modification of the process of FIG. 2, and in the FIG. 4 process, a part of the solid matter-containing aqueous solution taken out from the cooling and mixing vessel B is circulated again to the cooling and mixing vessel B.

Figure 5:
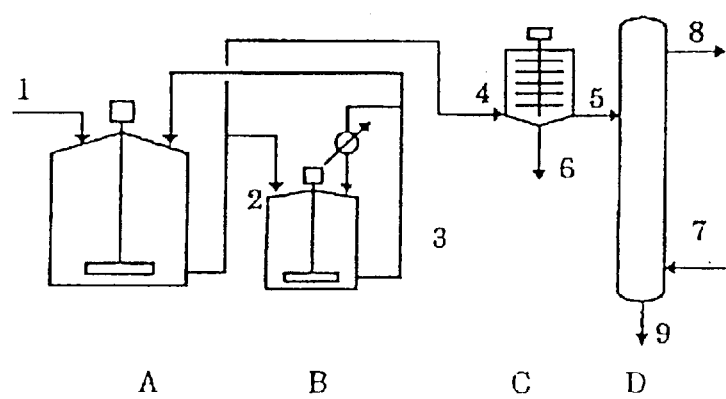

The process shown in FIG. 5 is a partial modification of the process of FIG. 3, and in the FIG. 5 process, a part of the solid matter-containing aqueous solution taken out from the cooling and mixing vessel B is circulated again to the cooling and mixing vessel B.

According to any one of the processes shown in FIGS. 2 to 5, the solid matter is deposited and thereafter the solid-containing aqueous methacrylic acid solution is taken out from the mixing vessel A and introduced into the separation apparatus C through the line 4 in which apparatus the solid matter is separated through a filter or the like, and then taken out through the line 6. The solid matter-free purified aqueous methacrylic acid solution is introduced through the line 5 into the extraction column D in which the methacrylic acid in the aqueous solution is extracted with an extracting solvent introduced through the line 7 and recovered through the line 8 while the waste water is discharged through the line 9.

The filter used in the separation apparatus C is not critical, and there can be used one which is 15 generally used for the separation of solid matter from a solution containing the solid matter. For example, a leaf filter, a cartridge filter, a decanter, a Nutsche funnel or the like can be used. Incidentally, as the filter used, a wire gauze of 110 to 360 mesh coated with diatomaceous earth (filter aid) having an average particle diameter of 10 to 50 μm is suitably used, whereby the solid matter deposited on the wire gauze can be easily removed together with the diatomaceous earth and wasted.

The structure of the above extraction column D, the conditions for the extraction and separation operation, the kind of the extracting solvent used and the like are not critical, and it is sufficient to use such apparatus and extracting solvent as generally used in the extraction and separation of methacrylic acid from an aqueous methacrylic acid solution and carry out the extraction and separation under conventional operation conditions. For example, it is sufficient to use, as the extracting solvent, an aromatic hydrocarbon (e.g. benzene or toluene), an ester (e.g. ethyl acetate or propyl acetate) or the like and contact the aqueous methacrylic acid solution with the extracting solvent at a temperature ranging from 15° to 50° C.

In the present invention, the impurities which cause such troubles as the generation of scum and the like in the extraction and separation step, can be effectively separated from the crude aqueous methacrylic acid solution, so that it is possible to further increase the degree of extraction of methacrylic acid by severely controlling the temperature conditions in the extraction and separation step.

The present invention has been explained above for a case of producing methacrylic acid. Similarly to the above case of producing methacrylic acid, acrylic acid can be obtained by cooling and condensing an acrylic acid-containing reaction product gas to obtain a crude aqueous acrylic acid solution, separating impurities as solid matter from the crude aqueous acrylic acid solution to obtain a purified aqueous acrylic acid solution, and then extracting and separating acrylic acid from the purified aqueous acrylic acid solution.

The present invention is more specifically described below based on Examples.

EXAMPLE 1

A methacrylic acid-containing reaction product gas obtained by the gas-phase catalytic oxidation of isobutylene was cooled and condensed. Then, low-boiling substances were removed from the resulting condensate to obtain a crude aqueous methacrylic acid solution. The methacrylic acid concentration of this solution was 42% by weight, and the amount of terephthalic acid dissolved in the supersaturation state in the aqueous solution was 900 ppm.

In a vessel was placed 100 ml of the above crude aqueous methacrylic acid solution. The solution was cooled to a temperature of 10° C. and stirred for 20 hours to deposit solid matter. 100 ml of this solid-containing aqueous solution was placed in a vessel containing 900 ml of the same crude aqueous methacrylic acid solution as mentioned above, to make a total volume of 1,000 ml. The resulting solution was stirred at 40° C. for 5 hours, and the solid matter deposited was removed by filtration. The amount of terephthalic acid dissolved in the resulting filtrate, namely, the purified aqueous methacrylic acid solution was 400 ppm.

EXAMPLE 2

Figure 1:
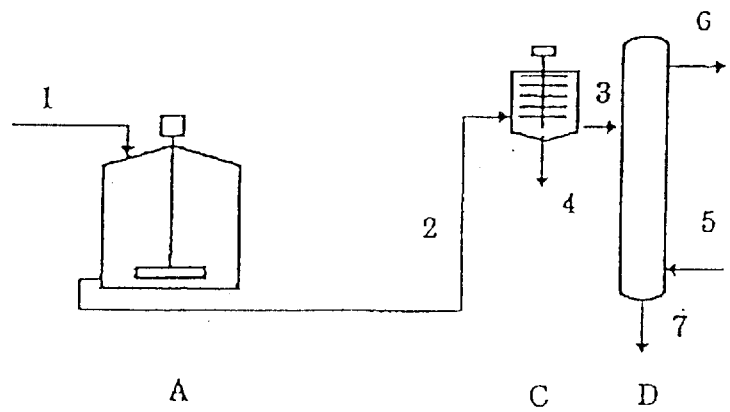
FIG. 1 is a diagram showing an embodiment of the apparatus (cooling, solid-liquid separation and extraction) for carrying out the present invention, and each of FIG. 2 to FIG. 5 is a diagram showing another embodiment of the apparatus for carrying out the present invention.

In the present Example, the same crude aqueous methacrylic acid solution as used in Example 1 was continuously treated in the apparatus shown in FIG. 1.

The crude aqueous methacrylic acid solution was introduced into the mixing vessel A through the line 1 and cooled and stirred therein under the conditions of normal pressure, a temperature of 35° C. and a residence time of 5 hours to deposit solid matter. This solid matter-containing aqueous methacrylic acid solution was introduced into a leaf filter C in which diatomaceous earth having an average particle diameter of 40 μm had been precoated on a wire gauze of 110 mesh, through the line 2 to remove the solid matter. The solid matter-free, purified aqueous methacrylic acid solution thus obtained was introduced, through the line 3, into the extraction column D (multi-stage extraction column) in which methacrylic acid was extracted and separated using toluene as an extracting solvent under the conditions of normal pressure and a temperature of 15° to 50° C.

The production of methacrylic acid was continuously conducted according to the above-mentioned procedure; however, no such troubles as deterioration of liquid-liquid separation and the like due to the generation of scum in the extraction column D were found for about 3 months.

The flow rates and compositions (concentrations of methacrylic acid, deposited terephthalic acid, water and the like) of the aqueous solutions in the main lines 1 to 3 are shown in Table 1.

TABLE 1

| Line No. | Flow rate (kg/Hr) | Methacrylic acid (wt. %) | Terephthalic acid (ppm) | | Water (wt. %) | Others (wt. %) |
| --- | --- | --- | --- | --- | --- | --- |
| | | | Dissolved | Deposited | | |
| 1 | 100 | 42 | 900 | — | 48 | 10 |
| 2 | 100 | 42 | 350 | 550 | 48 | 10 |
| 3 | 100 | 42 | 350 | — | 48 | 10 |

EXAMPLE 3

In the present Example, the same crude aqueous methacrylic acid solution as used in Example 1 was continuously treated in the apparatus shown in FIG. 2.

90% by weight of the crude aqueous methacrylic acid solution was introduced into the mixing vessel A through the line 1. Simultaneously therewith, 10% by weight of the crude aqueous methacrylic acid solution was introduced into the cooling and mixing vessel B through the line 2 and cooled and stirred therein under the conditions of normal pressure, a temperature of 10° C. and a residence time of 20 hours to deposit solid matter. This solid matter-containing aqueous methacrylic acid solution was circulated from the cooling and mixing vessel B to the mixing vessel A through the line 3.

In the mixing vessel A, a mixed aqueous solution consisting of the crude aqueous methacrylic acid solution introduced through the line 1 and the solid matter-containing aqueous methacrylic acid solution circulated through the line 3 was stirred under the conditions of normal pressure, a temperature of 40° C. and a residence time of 5 hours. The aqueous solution containing deposited solid matter was introduced, through the line 4, into the leaf filter C in which diatomaceous earth having an average particle diameter of 40 μm had been precoated on a wire gauze of 110 mesh, to remove the solid matter. The solid matter-free, purified aqueous methacrylic acid solution thus obtained was introduced into the extraction column D (multi-stage extraction column) through the line 5, and methacrylic acid was extracted and separated therein using toluene as an extracting solvent under the conditions of normal pressure and a temperature of 15° to 50° C.

The production of methacrylic acid was continuously conducted according to the above-mentioned procedure for about 3 months; however, there were found no such troubles as deterioration of liquid-liquid separation and the like due to the generation of scum in the extraction column D.

The flow rates and compositions (concentrations of methacrylic acid, deposited terephthalic acid, water and the like) of the aqueous solutions in the main lines 1 to 4 are shown in Table 2.

TABLE 2

| Line No. | Flow rate (kg/Hr) | Methacrylic acid (wt. %) | Terephthalic acid (ppm) | | Water (wt. %) | Others (wt. %) |
|---|---|---|---|---|---|---|
| | | | Dissolved | Deposited | | |
| 1 | 100 | 42 | 900 | — | 48 | 10 |
| 3 | 11 | 42 | 100 | 800 | 48 | 10 |
| 4 | 100 | 42 | 400 | 500 | 48 | 10 |
| 5 | 100 | 42 | 400 | — | 48 | 10 |

According to the present invention, the impurities contained in the crude aqueous (meth)acrylic acid solution obtained by cooling and condensing a (meth)acrylic acid-containing reaction product gas can be efficiently removed in a simple manner. Hence, various troubles caused by the impurities contained in the crude aqueous (meth)acrylic acid solution in the extraction and separation step can be effectively prevented, and (meth)acrylic acid can be extracted in a very high degree of extraction.

Further, according to the present invention, since the content of impurities (they are difficult to separate in a distillation and purification step) is reduced, (meth)acrylic acid can be produced at a high purity.

Furthermore, according to the present invention, even when a crude aqueous (meth)acrylic acid solution having a high (meth)acrylic acid concentration of 35 to 50% by weight is used, the impurities contained therein can be removed efficiently, so that the amount of the waste water generated in the extraction and separation step can be reduced.

What is claimed is:

1. A process for producing (meth)acrylic acid by gas-phase catalytic oxidation, which comprises cooling and condensing a (meth)acrylic acid-containing reaction product gas to obtain a crude aqueous (meth)acrylic acid solution; cooling the aqueous solution to deposit the impurities contained in the aqueous solution, as solid matter; separating the solid matter; and then extracting and separating (meth) acrylic acid from the purified aqueous (meth)acrylic acid solution obtained.

2. The process according to claim 1, wherein the crude aqueous (meth)acrylic acid solution is introduced into a mixing vessel and cooled therein at a temperature ranging from 5° to 50° C.

3. The process according to claim 1, wherein 3 to 30% by weight of the crude aqueous (meth)acrylic acid solution is introduced into a cooling and mixing vessel; simultaneously therewith, the remainder is introduced into a mixing vessel; the crude aqueous (meth)acrylic acid solution introduced into the cooling and mixing vessel is cooled therein at a temperature ranging from 0° to 30° C., and thereafter, a part or the whole of the solution is circulated to the mixing vessel.

4. The process according to claim 1, wherein the crude aqueous (meth)acrylic acid solution is introduced into a mixing vessel and stirred therein, then 3 to 30% by weight thereof is introduced into a cooling and mixing vessel and cooled therein at a temperature ranging from 0° to 30° C., and a part or the whole of the cooled solution in the cooling and mixing vessel is circulated to the mixing vessel.

5. The process according to any one of claims 1 to 4, wherein the (meth)acrylic acid concentration in the crude aqueous (meth)acrylic acid solution is 35 to 50% by weight.

\* \* \* \* \*